United States Patent [19]

Graham et al.

[11] Patent Number: 4,874,870

[45] Date of Patent: Oct. 17, 1989

[54] INTERMEDIATES FOR PREPARING HMG-COA REDUCTASE INHIBITORS

[75] Inventors: Samuel L. Graham, Harleysville; Thomas H. Scholz, Souderton, both of Pa.

[73] Assignee: Merck & Co., Inc., Rahway, N.J.

[21] Appl. No.: 231,321

[22] Filed: Aug. 12, 1988

Related U.S. Application Data

[62] Division of Ser. No. 65,223, Jun. 22, 1987, Pat. No. 4,795,811.

[51] Int. Cl.$^4$ .......................................... C07D 405/10
[52] U.S. Cl. ...................................... 548/336; 544/6; 544/58.4; 544/70; 544/139; 544/230; 544/370; 546/15; 546/199; 546/206; 548/327; 548/333; 548/341

[58] Field of Search ............... 548/336, 327, 333, 341; 544/6, 58.4, 70, 139, 230, 370; 546/15, 199, 206

[56] References Cited

PUBLICATIONS

H. Staab, *Angew. Chem. Internat. Edit.*, 1,351 (1962).
K. Ishizumi, et al., *Chem. Pharm. Bull.*, 16(3), 492 (1968).
Hajos, Complex Metal Hydrides, Elsevier Scientific Publishers, New York, 1979, pp. 49–55 and 333–337.

*Primary Examiner*—Richard A. Schwartz
*Attorney, Agent, or Firm*—Melvin Winokur; Joseph F. DiPrima

[57] ABSTRACT

A process for converting 6-carboxy to 6-hydroxymethyl mevinolin analogs and novel intermediates formed in this process are disclosed.

5 Claims, No Drawings

INTERMEDIATES FOR PREPARING HMG-COA REDUCTASE INHIBITORS

This is a division of application Ser. No. 065,223, filed June 22, 1987, now U.S. Pat. No. 4,795,811.

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occurring compounds and their semi-synthetic analogs have the following general structural formulae:

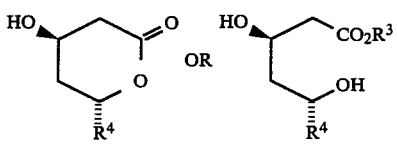

wherein:
$R^3$ is hydrogen, $C_{1-5}$ alkyl or $C_{1-5}$ alkyl substituted with a member of the group consisting of phenyl, dimethylamino, or acetylamino; and
$R^4$ is:

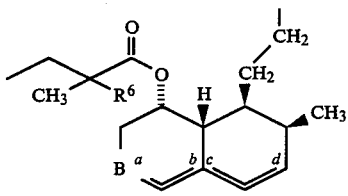

wherein B is $R^5$

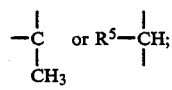

$R^5$ is H or OH; and
$R^6$ is hydrogen or methyl; and a, b, c, and d represent optional double bonds, especially where b and d represent double bonds or a, b, c, and d are all single bonds; provided that where a is a double bond, B is

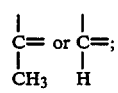

U.S. patent application Ser. No. 048,136, filed May 15, 1987, now abandoned, discloses biosynthetic and semisynthetic analogs of mevinolin and related compounds which possess a hydroxymethyl or a carbonyloxy group of structure $-CO_2R^3$ substituted on the 6-position of the polyhydronaphthyl moiety and wherein $R^4$ is

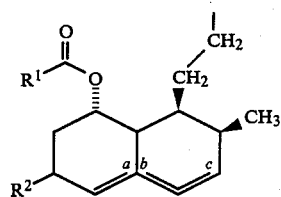

wherein
$R^1$ is a broadly-defined acyl side chain which includes, among other groups, substituted and unsubstituted $C_{1-10}$ alkyl, $C_{1-10}$ alkoxy, $C_{1-10}$ alkenyl, $C_{3-8}$ cycloalkyl and phenyl;
$R^2$ is $CH_2OH$ or $CO_2R^3$; and
$R^3$ is hydrogen, 2,3-dihydroxypropyl, $C_{1-5}$ alkyl, $C_{1-5}$ alkyl substituted with a member of the group consisting of phenyl, dimethylamino, or acetylamino;
a, b, and c each represent single bonds or one of a, b, and c represents a double bond or both a and c represent double bonds;

Said 6-hydroxymethyl and 6-carbonyloxy derivatives of mevinolin and analogs thereof are useful in treating hypercholesterolemia. However, comparative test data indicate that the 6-hydroxymethyl mevinolin analogs have a greater HMG-CoA reductase inhibiting effect than the 6-carboxy compounds. Thus there is a real need for the conversion of the 6-carboxy substituent into a 6-hydroxymethyl substituent in a minimum number of steps and without affecting the variety of other functionalities in the compound under conversion.

SUMMARY OF THE INVENTION

This invention relates to novel intermediates (II) useful in the preparation of 6-desmethyl-6-hydroxymethyl derivatives of mevinolin and analogs thereof (III), wherein the 8-acyl

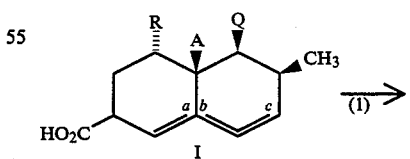

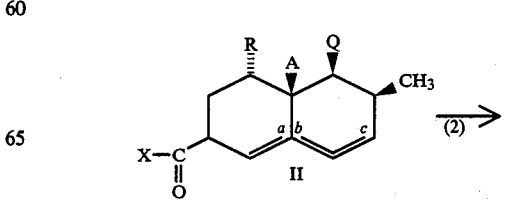

-continued

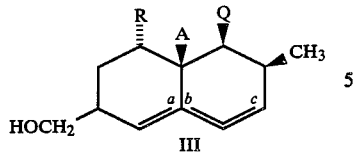

side chain and the degree of unsaturation within the polyhydronaphthyl ring are varied. The invention also includes novel processes (1) and (2) for converting a 6-carboxy group to a 6-hydroxymethyl substituent without chemically altering any of the other labile functionalities nor any stereochemistry within a compound of formula (I).

DESCRIPTION OF THE INVENTION

This invention relates to novel intermediates II, a novel process (1) for the preparation of intermediates (II), and a novel process (2) for the preparation from said intermediates of 6-desmethyl-6-hydroxymethyl derivatives of mevinolin and analogs III thereof wherein the 8-acyl side chain and the degree of unsaturation within the polyhydronaphthyl ring are varied.

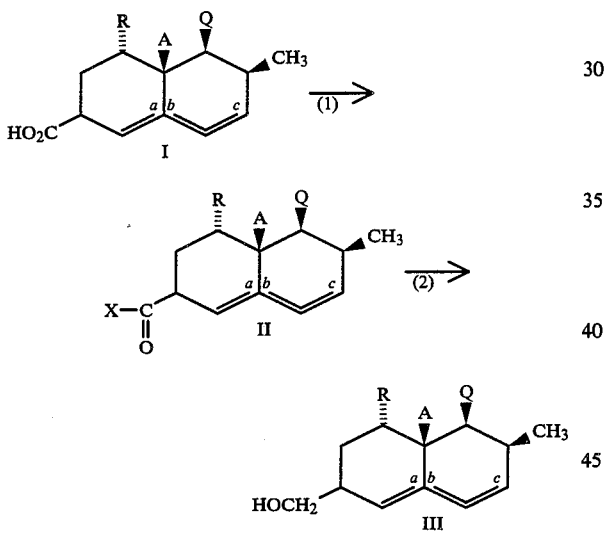

Using the novel processes of this invention, the reduction of the 6-carboxyl group is accomplished without chemically altering any of the other labile functionalities nor any stereochemistry within a compound of formula (I). Indeed the total process permits the desired reduction without the necessity of protecting and deprotecting any other functionality within compounds (I) or (II).

The intermediates (II) of the instant invention are prepared in a novel process (1) which comprises: reacting the compound (I)

wherein a, b, and c represent single bonds or one of a, b, or c represents a double bond or both a and c represent double bonds; and wherein Q is selected from a group consisting of:

(a) [structure with HO, O, $CH_2CH_2$—]

(b) $CH_2CH_2CN$;

(c) [structure: $(CH_2)_z$—C(H)(O—$P_2$)(O—$P_1$)]

wherein z is 0 or 2 and $P_2$ and $P_1$ are independently lower alkyl or $P_2$ and $P_1$ together with the oxygens to which they are attached and the carbon bonded to the oxygens form a ring of 5 to 8 atoms; and wherein A is H or OH; and wherein R is:

$$R_5-\left[\begin{array}{c} R_3 \\ | \\ C \\ | \\ R_4 \end{array}\right]_n \begin{array}{c} R_1 \; O \\ | \; \| \\ C-C-O-, \\ | \\ R_2 \end{array}$$

wherein:

n is 0 to 5

$R_1$ and $R_2$ independently are hydrogen, $C_{1-5}$ alkyl, or $R_1$ and $R_2$ together with the carbon atom to which they are attached from a carbocyclic ring of 3 to 8 carbon atoms;

$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when n is 2 to 5, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;

$R_5$ is hydrogen, halogen, hydroxy, $C_{1-5}$ alkyl, phenyl or substituted phenyl in which the substituents are V and W, or $R_5$ is a group selected from:

(a) $C_{1-5}$ alkylthio or phenylthio or substituted phenylthio in which the substituents are V and W;

(b) $C_{1-5}$-alkanoyloxy-$C_{1-4}$-alkyl;

(c) $R_6-O-\overset{\underset{\|}{O}}{C}-(CH_2)_m$ in which m is 0 to 3 and $R_6$ is $C_{1-5}$ alkyl;

(d) $R_7R_8N\overset{\underset{\|}{O}}{C}-(CH_2)_m$ in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperazinyl or thiomorpholinyl;

(e) 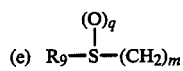

in which q is 0 to 2 and $R_9$ is $C_{1-5}$ alkyl or phenyl or substituted phenyl in which the substituents are V and W;

V and W independently are hydrogen, halogen, hydroxy, trifluoromethyl, $C_{1-3}$ alkyl, $C_{1-3}$ alkyloxy or hydroxy-$C_{1-3}$ alkyl;

with a compound known to activate carboxylic acids towards relatively mild reducing agents and other nucleophiles, such as:
- (i) a N,N'-carbonyl diazole, such as N,N'-carbonyldiimidazole or N,N'-carbonyldibenzimidazole or N,N'-carbonylbenzotriazole;

(ii) 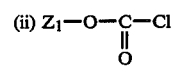

wherein $Z_1$ is $C_{1-5}$ alkyl; and triethylamine; or
- (iii) a N-hydroxyamine such as N-hydroxysuccinimide or N-hydroxybenzotriazole in the presence of a diimide such as dicyclohexylcarbodiimide or N-ethyl-N'-(N,N-dimethylaminopropyl)-carbodiimide hydrochloride;

in an inert solvent, to yield compound (II)

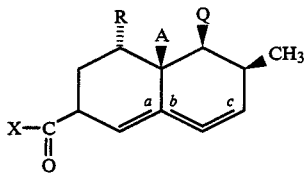

wherein X is selected from
(i) an azole such as:

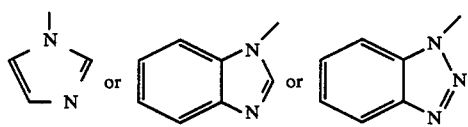

(ii) 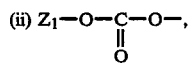

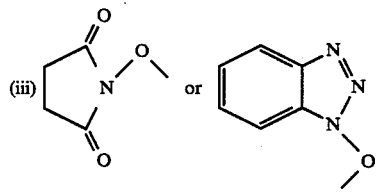

The intermediates (II) are used to form the 6-desmethyl-6-hydroxymethyl mevinolin analogs (III) in a novel process (2) which comprises: reacting the compound (II) with a hydride reagent such as an alkali metal borohydride, particularly NaBH$_4$ and the like, in a suitable solvent to obtain compound (III).

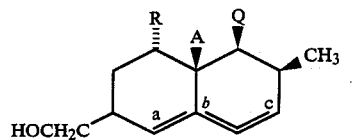

One embodiment of this invention is the compounds of formula (II).

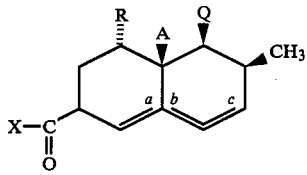

In one class of this embodiment are the compounds of formula (II) wherein R is

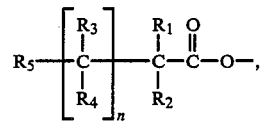

n is 0 to 3, $R_1$ is methyl, $R_2$ is hydrogen or methyl, A is hydrogen, Q is

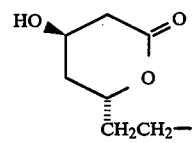

and a and c are double bonds or one of a, b or c is a double bond or a, b and c all represent single bonds. In a subclass of this embodiment are the compounds of formula (II) wherein X is

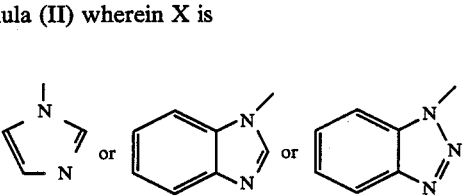

Exemplifying this subclass is:
(1) 6(R)-[2-[8(S)-(2,2-dimethylbutyryloxy)-2(S)-methyl-6(S)-(1-imidazolylcarbonyl)-1,2,6,7,8,8a(R)-hexahydronaphthyl-1(S)]ethyl]-4(R)-hydroxy-3,4,5,6-tetrahydro-2H-pyran-2-one.

In a second subclass are the compounds wherein X is

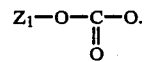

Exemplifying this subclass is:
(1) 6(R)-[2-[8(S)-(2,2-dimethylbutyryloxy)-2(S)-methyl-6(S)-(isobutyloxycarbonyloxycarbonyl)-1,2,6,7,8,8a(R)-hexahydronaphthyl-1(S)]ethyl]-4(R)-hydroxy-3,4,5,6-tetrahydro-2H-pyran-2-one.

In a second class of this embodiment R is

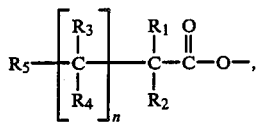

n is 0 to 3,

R₁ is methyl, R₂ is hydrogen or methyl, A is hydrogen and Q is

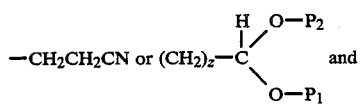

a and c are double bonds, or one of a, b or c is a double bond or a, b and c all represent single bonds. In a subclass of this embodiment are the compounds of formula (II) wherein X is

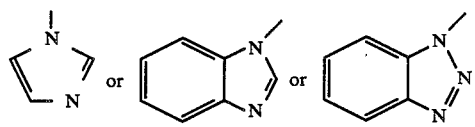

Exemplifying this subclass is:
(1) 1(S)-(2-cyanoethyl)-8(S)-(2,2-dimethylbutyryloxy)-6(S)-(1-imidazoylcarbonyl)-2(S)-methyl-1,2,6,7,8,8a(R)-hexahydronaphthalene; and
(2) 1(S)-(3,3-dimethoxypropyl)-8(S)-(2,2-dimethylbutyryloxy)-6(S)-(1-imidazoylcarbonyl)-2(S)-methyl-1,2,6,7,8,8a(R)-hexahydronaphthalene.

In a second subclass, are the compounds wherein X is

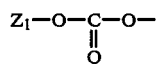

Exemplifying this subclass is:
(1) 1(S)-(2-cyanoethyl)-8(S)-(2,2-dimethylbutyryloxy)-6(S)-(isobutyloxycarbonyloxycarbonyl)-2(S)-methyl-1,2,6,7,8,8a(R)-hexahydronaphthalene, and
(2) 1(S)-(3,3-dimethoxypropyl)-8(S)-(2,2-dimethylbutyryloxy)-6(S)-(isobutyloxycarbonyloxycarbonyl)-2(S)-methyl-1,2,6,7,8,8a(R)-hexahydronaphthalene.

A second embodiment of this invention is the process (1) for the preparation of intermediates (II) from the 6-carboxy substituted starting materials.

A compound of formula I is reacted with a compound known to activate carboxylic acids towards relatively mild reducing agents.

In one class of this embodiment a compound of formula (I) is contacted with a N,N-carbonyldiazole such as N,N'-carbonyldimidazole or N,N'-carbonyldibenzimidazole or N,N'-carbonylbenzotriazole, at a temperature between −75° and 0° C.

In a second class a compound of formula (I) is contacted with an alkyl chloroformate such as isobutyl chloroformate, at a temperature between −75° and 0° C.

In a third class, a compound of formula (I) is contacted with a N-hydroxyamine such as N-hydroxysuccinimide or N-hydroxybenzotriazole in the presence of a diimide.

A third embodiment of this invention is the process (2) for the conversion of compounds of formula (II) to compounds of formula (III). This process consists of contacting a compound of formula (II) with a mild reducing agent in a polar solvent to form product compound (III).

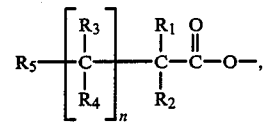

A preferred mild reducing agent for this process is an alkali metal borohydride, particularly sodium borohydride.

In one class of this embodiment the process yields compounds (III) wherein R is

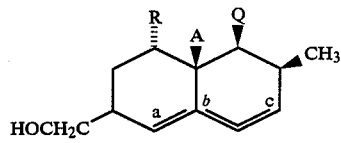

n is 0 to 3, R₁ is methyl, R₂ is hydrogen or methyl, A is hydrogen, and a and c are double bonds or one of a, b or c is a double bond or a, b and c are all single bonds. In one subclass are the compounds wherein Q is:

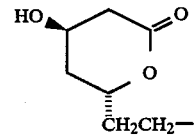

Exemplifying this subclass is
(1) 6(R)-[2-[8(S)-(2,2-dimethylbutyryloxy)-6(S)-hydroxymethyl-2(S)-methyl-1,2,6,7,8,8a(R)-hexahydronaphthyl-1(S)]ethyl]-4(R)-hydroxy-3,4,5,6-tetrahydro-2H-pyran-2-one.

In a second subclass are the compounds wherein Q is:

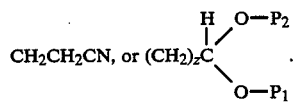

Exemplifying this subclass are
(1) 1(S)-(2-cyanoethyl)-8(S)-(2,2-dimethylbutyryloxy)-6(S)-hydroxymethyl-2(S)-methyl-1,2,6,7,8,8a(S)-hexahydronaphthalene; and
(2) 1(S)-(3,3-dimethyoxypropyl)-8(S)-(2,2-dimethylbutyryloxy)-6(S)-hydroxymethyl-2(S)-methyl-1,2,6,7,8,8a(S)-hexahydronaphthalene.

The reaction of a compound of formula (I) with a N,N'-carbonyl diazole is conducted at a temperature between −20° and +20° C., preferably at 0° C. for a period of from 1 to 12 hours, most preferably 2 hours at 0° C., in the presence of an inert solvent under an inert atmosphere. Illustrative of such inert solvents are methylene chloride, tetrahydrofuran and the like. The inert atmosphere may be nitrogen or argon.

The reaction of a compound of formula (I) with an alkyl chloroformate is conducted at a temperature between −70° and 0° C., preferably at −70° C. for a period of from 10 minutes to 120 minutes, most preferably 30 minutes at −70° C., in the presence of a trialkylamine, such as triethylamine, and an inert solvent, followed by warming to 0°.

The reaction of a compound of formula (I) with a N-hydroxyamine can be carried out using dicyclohexylcarbodiimide as a coupling aid.

The reduction of a compound of formula (II) wherein X is an azole is conducted using sodium borohydride and degassed dimethylformamide. The reaction is carried out at a temperature between 0° and 25° C., preferably at 0° C. for a period of from 15 minutes to 120 minutes, most preferably 30 minutes at 0° C. also in the presence of the same solvent as the reaction of compound (I) with a carbonyl diazole.

The reduction of a compound of formula (II) wherein X is oxycarbonyloxyalkyl, is conducted using a solution of $NaBH_4$ in absolute ethanol. The reaction is carried out a temperature between −10° and 25° C., preferably at 0° C. for a period of from 1 to 30 minutes, most preferably 10 minutes at 0° C., in the presence of the same solvent as the reaction of compound (I) with the alkyl chloroformate.

The starting compounds (I) of the instant invention where Q is the lactone ring are prepared according to the procedures detailed in European Pat. No. 0251,625, published January 7, 1988, which procedures are hereby incorporated by reference and in abandoned U.S. patent application Ser. No. 048,136 filed May 15, 1987.

The compounds in U.S. patent application Ser. No. 048,136, filed May 15, 1987, are represented by the following general structural formulae (I) and (II):

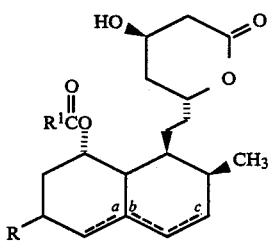
(I)

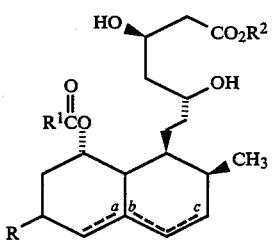
(II)

wherein:
R is

$R^1$ and $R^3$ are independently selected from:

(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$ in which n is 0 to 2,
 (j) $C_{3-8}$ cycloalkylS(O)$_n$,
 (k) phenylS(O)$_n$,
 (l) substituted phenylS(O)$_n$ in which the substituents are X and Y, and
 (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
 (a) $C_{1-10}$ alkyl
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy
  (vi) phenyl,
  (vii) substituted phenyl in which the substituents are X and Y
  (viii) $C_{1-10}$ alkylS(O)$_n$,
  (ix) $C_{3-8}$ cycloalkylS(O)$_n$,
  (x) phenylS(O)$_n$,
  (xi) substituted phenylS(O)$_n$ in which the substituents are X and Y, and
  (xii) oxo,
 (c) $C_{1-10}$ alkylS(O)$_n$,
 (d) $C_{3-8}$ cycloalkylS(O)$_n$,
 (e) phenylS(O)$_n$,
 (f) substituted phenylS(O)$_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl, (c) piperazinyl,
(d) morpholinyl, and
(e) thiomorpholinyl; and
(17) $R^5S$ in which $R^5$ is selected from
  (a) $C_{1-10}$ alkyl,
  (b) phenyl, and
  (c) substituted phenyl in which the substituents are X and Y;
$R^2$ and $R^4$ are independently selected from:
(a) hydrogen;
(b) $C_{1-5}$ alkyl;
(c) substituted $C_{1-5}$ alkyl in which the substituent is selected from
  (i) phenyl,
  (ii) dimethylamino, and
  (iii) acetylamino, and
(d) 2,3-dihydroxypropyl;
$R^6$ and $R^7$ are independently selected from:
(1) hydrogen;
(2) $C_{1-10}$ alkyl;
(3) substituted $C_{1-10}$ alkyl in which one or more substituent(s) is selected from
  (a) halogen,
  (b) hydroxy,
  (c) $C_{1-10}$ alkoxy,
  (d) $C_{1-10}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkyl $S(O)_n$ in which n is 0 to 2,
  (j) $C_{3-8}$ cycloalkyl $S(O)_n$,
  (k) phenyl $S(O)_n$,
  (l) substituted phenyl $S(O)_n$ in which the substituents are X and Y, and
  (m) oxo;
(4) $C_{2-10}$ alkenyl;
(5) $C_{3-8}$ cycloalkyl;
(6) aminocarbonyl;
(7) substituted aminocarbonyl in which one or more substituent(s) is selected from
  (a) $C_{1-5}$ alkyl,
  (b) $C_{3-8}$ cycloalkyl,
  (c) phenyl,
  (d) substituted phenyl in which the substituents are X and Y;
(8) phenyl;
(9) substituted phenyl in which the substituents are X and Y;
(10) $C_{1-10}$ alkylcarbonyl;
(11) $C_{3-8}$ cycloalkylcarbonyl;
(12) phenylcarbonyl;
(13) substituted phenylcarbonyl in which the substituents are X and Y; and
(14) a nitrogen-containing heterocyclic group such as piperidinyl, pyrrolidinyl, piperazinyl, morpholinyl or the like formed by joining the substituents $R^6$ and $R^7$ to form a heterocyclic ring; and
X and Y independently are hydrogen, halogen, trifluoromethyl, $C_{1-3}$ alkyl, nitro, cyano or group selected from:
(a) $R^8O(CH_2)_m$ in which m is 0 to 3 and $R^8$ is hydrogen, $C_{1-3}$alkyl or hydroxy-$C_{2-3}$alkyl;

(b) $$R^9\overset{O}{\underset{\|}{C}}O(CH_2)_m \text{ or } R^9O\overset{O}{\underset{\|}{C}}O(CH_2)_m$$

in which $R^9$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$alkylamino-$C_{1-3}$alkyl or di(hydroxy-$C_{2-3}$alkyl)amino-$C_{1-3}$alkyl;

(c) $$R^{10}O\overset{O}{\underset{\|}{C}}(CH_2)_m$$

in which $R^{10}$ is hydrogen, $C_{1-3}$alkyl, hydroxy-$C_{2-3}$alkyl, $C_{1-3}$alkoxy-$C_{1-3}$alkyl, phenyl or naphthyl;

(d) $$R^{11}R^{12}N(CH_2)_m, R^{11}R^{12}N\overset{O}{\underset{\|}{C}}(CH_2)_m$$
$$\text{or } R^{11}R^{12}N\overset{O}{\underset{\|}{C}}O(CH_2)_m$$

in which $R^{11}$ and $R^{12}$ independently are hydrogen, $C_{1-3}$alkyl, hydroxy-$C_{2-3}$alkyl or together with the nitrogen atom to which they are attached form a heterocyclic group selected from piperidinyl, pyrrolidinyl, piperazinyl, morpholinyl or thiomorpholinyl;
(e) $R^{13}S(O)_n(CH_2)_m$ in which $R^{13}$ is hydrogen, $C_{1-3}$alkyl, amino, $C_{1-3}$alkylamino or di($C_{1-3}$alkyl)amino; and a, b and c each represent single bonds or one of a, b and c represents a double bond or both a and c represent double bonds;
or a pharmaceutically acceptable salt thereof.

The compounds of formulae (I) and (II) wherein a and c represent double bonds are conveniently prepared from mevinolin or its analogs having a 6-methyl group by one of three methods:
  (a) adding the substrate to a growing culture of *Nocardia autotrophica* for a suitable incubation period followed by isolation, and derivatization if desired;
  (b) collecting a culture of the bioconverting microorganism and contacting the collected cells with the substrate; or
  (c) preparing a cell-free, enzyme-containing extract from the cells of the bioconverting microorganism and contacting this extract with the substrate.

Cultivation of the bioconverting microorganism of the genus Nocardia can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may equally be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected, preferably, are then washed with a suitable washing liquid, such as physiological saline or an appropriate buffer solution.

Contact of the collected cells of the microorganism of the genus Nocardia with the substrate is generally effected in an aqueous medium, for example in a phosphate buffer solution at a pH value of from 5 to 9. The reaction temperature is preferably within the range from 20° to 45° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the microorganism (which may, of course, vary from species to species and will also, as explained above, depend upon the cultivation time) and other factors.

The cell-free, enzyme-containing extract employed in method (c) may be obtained by breaking down the whole cells of the microorganism obtained as described in relation to method (b) by physical or chemical means, for example by grinding or ultrasonic treatment to provide a disintegrated cellular mass or by treatment with a surface active agent or an enzyme to produce a cellular solution. The resulting cell-free extract is then contacted with the substrate under the same conditions as are described above in relation to method (b).

The microorganism useful in the novel process of this invention is of the genus Nocardia. Of particular importance are the known strains of microorganism, *Nocardia autotrophica*, subspecies *canberrica*, ATCC 35203 of the culture MA-6181 and subspecies *amethystina* ATCC 35204 of the culture MA-6180 of the culture collection of Merck & Co., Inc., Rahway, New Jersey. It should be noted that the culture MA-6180 preferentially affords the hexahydronaphthyl compounds (a and c are double bonds) of this invention wherein R is $CH_2OH$, although the compounds wherein R is $CO_2H$ are also formed. Additionally, when the culture MA-6181 is utilized in the bioconversion reaction, the compounds of the invention wherein R is $CO_2H$ are preferentially formed, although the compounds wherein R is $CH_2OH$ are also prepared. A sample of the culture designated ATCC 35203 and ATCC 35204 is available in the permanent culture collection of the American Type Culture Collection at 12301 Parklawn Drive, Rockville, MD 20852.

A novel microorganism deposited in the culture collection of Merck & Co., Inc. and designated MA-6455 may also be utilized in the bioconversion reaction.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography, (for example on silica gel or alumina) and eluting the column with an appropriate eluent, especially in an HPLC apparatus.

The compounds of formula (I) wherein a and c represent double bonds and R is $CO_2H$ can be converted cleanly, and without epimerization of the methine group to which R is appended, to the corresponding primary alcohols wherein R is $CH_2OH$ as illustrated in the following synthetic pathway:

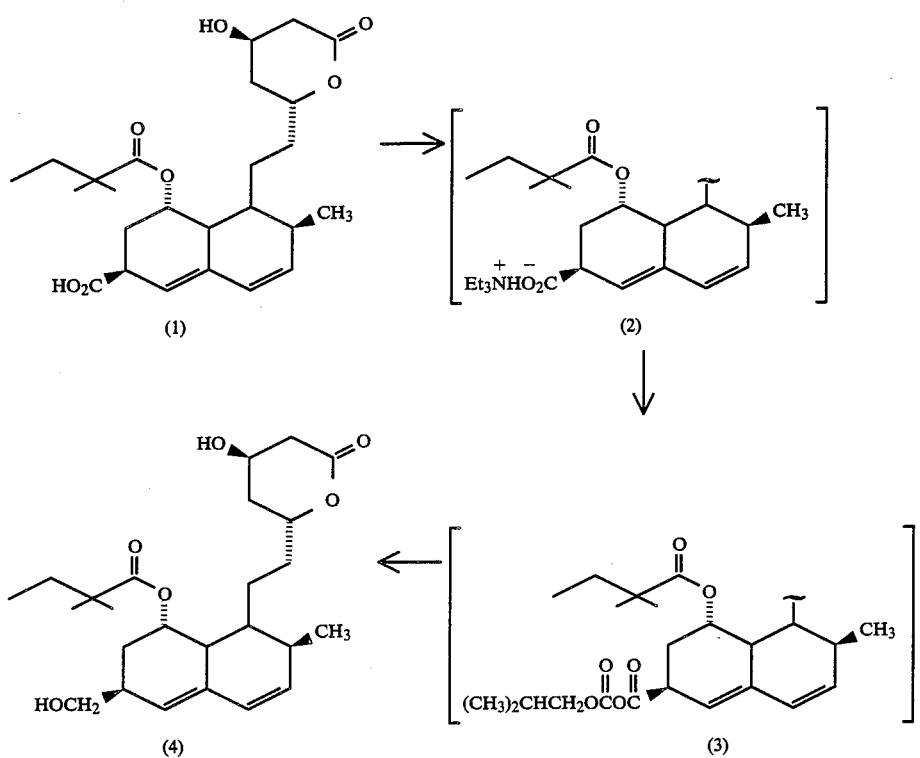

Compound (1) is converted to the corresponding triethylammonium salt (2) in a suitable organic solvent, preferably methylene chloride at room temperature. Without isolation but with cooling, preferably to −70° C., compound (2) is allowed to react with isobutyl chloroformate to afford the mixed anhydride (3). The resulting, cold solution of compound (3) is added to a cold, preferably 0° C., solution of a suitable reducing agent, such as sodium borohydride, in a suitable organic solvent, such as ethanol, to afford compound (4). This synthetic pathway also can be applied to the compounds of formula (I) wherein R is $CO_2H$ and a, b and c each represent single bonds or one of a, b and c represents a double bond.

The compounds of formulae (I) and (II) wherein a, b and c all represent single bonds are conveniently prepared from mevinolin via the following synthetic pathway:

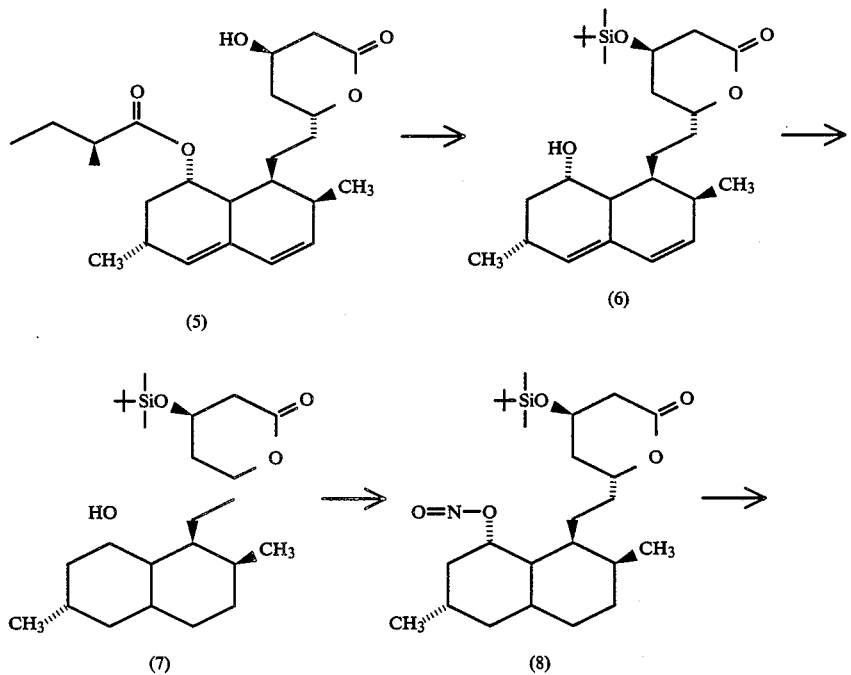

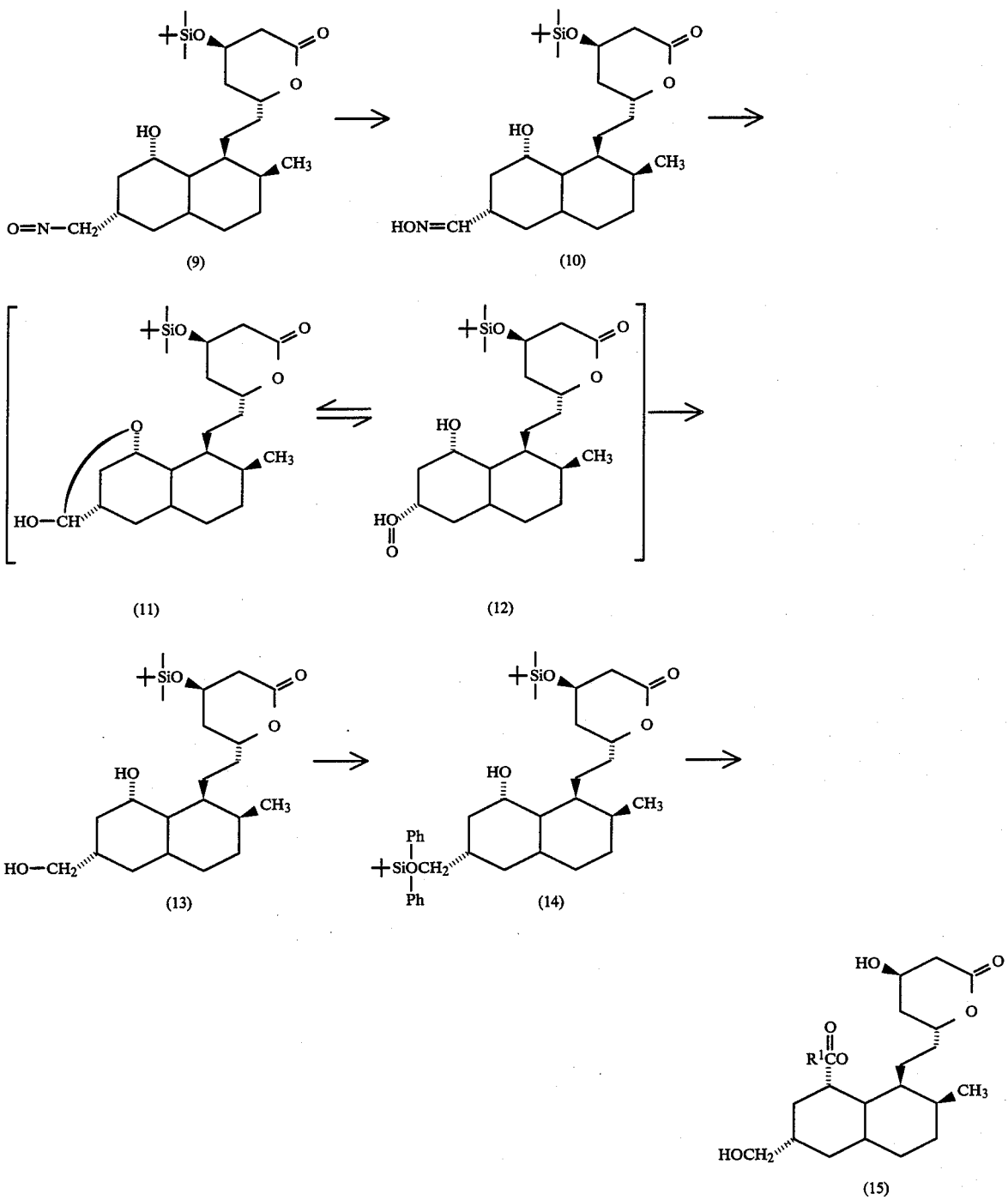

The starting material, mevinolin (5) is readily available or may be prepared according to the fermentation procedures disclosed in U.S. Pat. No. 4,231,938. The compound of the formula (5) is hydrolyzed under the conditions disclosed in U.S. Pat. No. 4,444,784 and then the 4-hydroxy function in the lactone moiety is protected with a suitable protecting group, exemplified here as a t-butyldimethylsilyl group, according to the procedure disclosed in U.S. Pat. No. 4,444,784 to yield the compound (6). Compound (6) is then hydrogenated under the analogous conditions disclosed in U.S. Pat. No. 4,351,844 to afford the compound (7). The compound (7) is then treated with nitrosyl chloride in the presence of a base, such as a trialkylamine, specifically, trimethylamine, triethylamine, pyridine, N,N-dimethylbenzylamine and the like, to afford the compound (8). The compound (8) is then subjected to a photo-rearrangement to give the compound (9). The compound (9) is heated to reflux in a protic solvent such as isopropanol and the like to yield the compound (10). The compound (10) is converted into the compound (11) by treatment with an alkali metal nitrite, such as sodium nitrite or potassium nitrite, in an aqueous organic acid such as acetic acid, propionic acid or the like. Compound (11), which is a hemiacetal, is in equilibrium with the hydroxy aldehyde, compound (12). This equilibrium mixture of compound (11) and compound (12) is treated with a reducing agent, such as sodium borohydride, to afford the compound (13). The hydroxymethyl group at the 6-position of the polyhydronaphthyl moiety is then protected with a suitable protecting agent, exemplified here as a t-butyldiphenylsilyloxy group. The resultant compound (14) is acylated under suitable conditions utilizing the appropriate alkanoyl halide or alkanoic acid, followed by the hydrolysis of the protecting groups to arrive at the compounds of the formula (15).

The compounds of the formula (I) wherein R is $CO_2H$ are conveniently prepared from the corresponding hydroxymethyl containing compound under mild oxidation conditions. The compounds of the formula (15) are treated with tris(triphenylphosphine)ruthenium (II) chloride to afford the 6-formyl derivative which is then treated with sodium chlorite and sulfamic acid to give the desired products.

The compounds of the formulae (I) and (II) wherein a represents a double bond are conveniently prepared from the compound of the formula (6) by the hydrogenation procedure using Wilkinson's catalyst as disclosed in U.S. Pat. No. 4,444,784 and subjecting the resultant 6(R)-[2-[8(S)-hydroxy-2(S),6(R)-dimethyl-1,2,3,4,5,7,8,8a(R)-octahydronaphthyl-1(S)]ethyl]-4(R)-(t-butyldimethylsilyloxy)-3,4,5,6-tetrahydro-2H-pyran-2-one to the above noted reaction sequence.

The compounds of the formulae (I) and (II) wherein b represents a double bond are conveniently prepared using an analogous reaction sequence but utilizing 6(R)-[2-[8(S)-hydroxy-2(S),6(R)-dimethyl-1,2,3,5,6,7,8,8a(R)-octahydronaphthyl-1(S)]ethyl]-4(R)-(t-butyldimethylsilyloxy)-3,4,5,6-tetrahydro-2H-pyran-2-one in place of the compound of the formula (7). This starting material may be prepared according to the procedures disclosed in U.S. Pat. No. 4,444,784.

The compounds of the formulae (I) and (II) wherein c is a double bond are conveniently prepared using an analogous reaction sequence but utilizing 6(R)-[2-[8(S)-hydroxy-2(S),6(S)-dimethyl-1,2,4a-(R),5,6,7,8,8a(S)-octahydronaphthyl-1(S)]ethyl]-4(R)-(t-butyldimethylsilyloxy)-3,4,5,6-tetrahydro-2H-pyran-2-one in place of the compound of the formula (7). This starting material may be prepared from the natural fermentation product prepared according to the procedures disclosed in U.S. Pat. No. 4,294,846.

The compounds (15) of the formulae (I) wherein R is $CH_2OH$, and which are prepared as illustrated in the preceeding synthetic pathway, each have the $CH_2OH$ group appended to the polyhydronaphthalene ring as a 6α-substituent. The corresponding 6β-epimers are conveniently prepared via the following synthetic pathway:

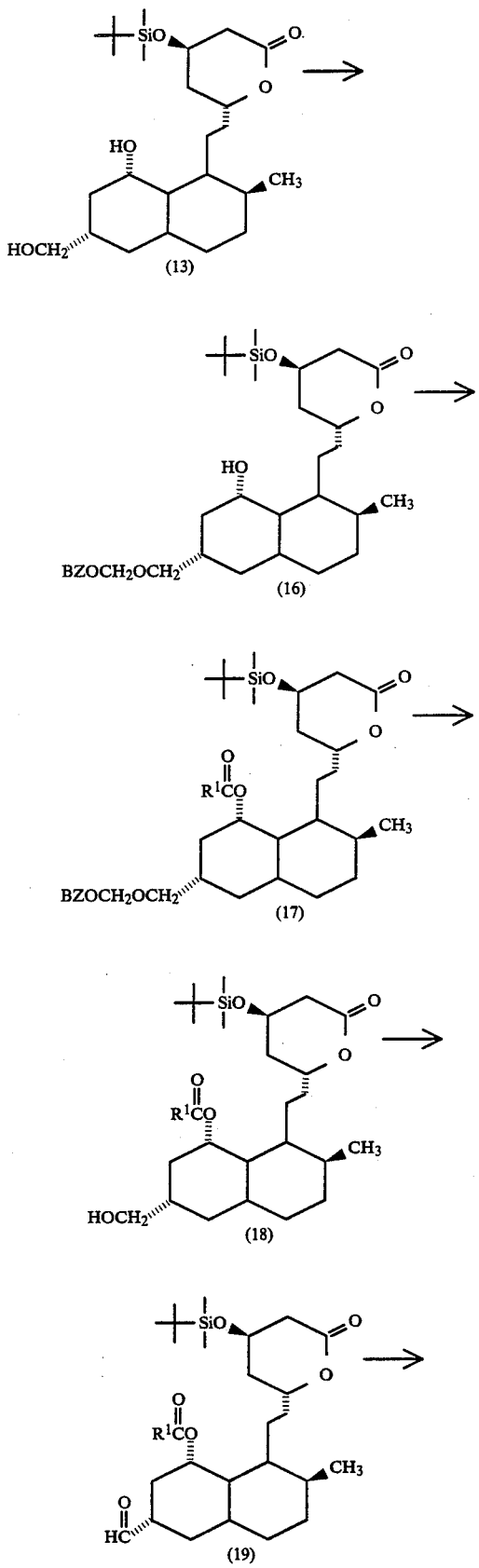

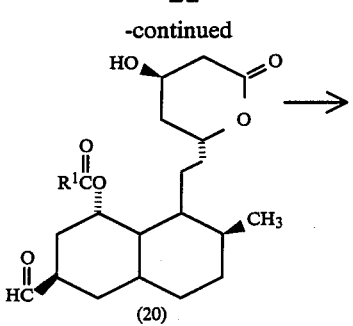

(20)

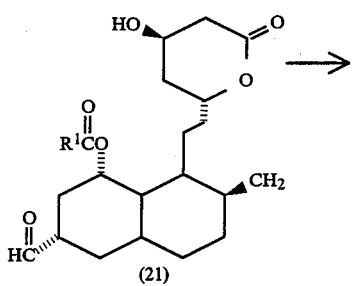

(21)

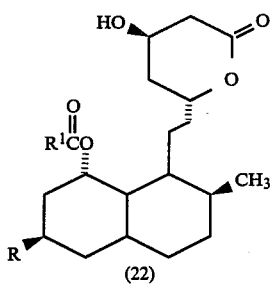

(22)

a, R = CH₂OH
b, R = CO₂H

Compound (13), an intermediate in the preceeding synthetic pathway, is converted to compound (16) by treatment with benzyl chloromethyl ether in the presence of a suitable base such as a trialkylamine, preferably diisopropylethylamine, in a suitable organic solvent such as methylene chloride in the cold, preferably at about 0° C. Compound (16) is acylated as described for compound (14) to afford compound (17). Removal of the benzyloxymethyl protecting group from compounds (17) via catalytic hydrogenation under standard conditions provides compounds (18). The latter are oxidized to compounds (19) by standard methods, including the method of Swern involving the use of oxalyl chloride and dimethyl sulfoxide in methylene chloride followed by triethylamine. Treatment of compounds (19) under the conditions (i.e., tetra-n-butylammonium fluoride in THF buffered with HOAc) used to deblock the tert-butyldimethylsilyl ether (14) serves both to deblock this protecting group in compounds (19) and to epimerize the resulting 6α-aldehydes (21) to afford a mixture of epimeric compounds (20) and (21), the ratio of the 6β-epimer to the 6α-epimer being determined by the exact reaction conditions used in each instance. After isolation by chromatography on a suitable support such as silica gel and the like, compounds (20) can be converted to compounds (22a) and (22b) by reduction with a suitable reducing agent such as sodium borohydride and oxidation with a suitable oxidant such as sodium chlorite in the presence of sulfamic acid, respectively. In addition, compounds (22b) can be converted cleanly to compounds (22a) using the procedures presented in the first synthetic pathway.

Alternatively, the appropriate dihydro or tetrahydro derivative of mevinolin may be subjected to one of the microbiological methods described above to afford the compounds of the formulae (I) and (II), wherein R is CH₂OH or CO₂H.

The starting compounds (I) wherein Q is CH₂CH₂CN, and c is a double bond are prepared from the corresponding aldehydes employing standard chemical transformations. The aldehyde may be prepared following the procedure described by Davidson et.al, J. Chem. Soc., Chem. Comm., 1662 (1985). Conversion of compounds (I) wherein c is a double bond to those wherein a and c are double bonds may be accomplished by bromination followed by dehydrobromination using the procedure described by Funk and Zeller, J. Org. Chem., 47, 180 (1982). Compounds (I) wherein a or b is a double bond or a, b, and c are all single bonds can be prepared from the diene by hydrogenation following the procedures disclosed in U.S. Pat. No. 4,351,844. Alternatively where a, b and c are all single bonds or a or b is a double bond the aldehyde may be prepared following the procedures described by Funk and Zeller (W. E. Zeller Ph.D. Thesis, University of Nebraska 1985) or the procedure of Deutsch and Snider, Tetrahedron Lett. 24, 3701, (1983).

Starting compounds (1) where Q is

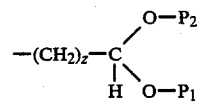

are prepared from the corresponding aldehydes employing standard chemical transformations. The aldehydes are prepared following the procedures described above.

The appropriately substituted acyl chlorides for esterifying the C-8-position of the polyhydronaphthyl moiety are commercially available or prepared from known starting materials.

The following Examples illustrate the present invention and as such are not to be considered as limiting the invention set forth in the claims appended hereto.

EXAMPLE 1

Preparation of 6(R)-[2-[8(S)-(2,2-dimethylbutyryloxy)-2(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2one (a)

6(R)-[2-[8(S)-(2,2-dimethylbutyryloxy)-2(S)-methyl-6(S)-isobutyloxycarbonyloxycarbonyl-1,2,6,7,8,8a(R)-hexahydronaphthyl-1(S)]ethyl]-4(R)-hydroxy-3,4,5,6-tetrahydro-2H-pyran-2-one To a solution of 102 mg (0.23 mmol) 6(R)-[2-[8(S)-(2,2-dimethylbutyryloxy)-2(S)-methyl-6(S)-carboxy-1,2,6,7,8,8a(R)-hexahydronaphthyl-1(S)]ethyl]-4(R)-hydroxy-3,4,5,6-tetrahydro-2H-pyran-2-one in 2.3 ml of dry (4A° molecular sieves) CH₂Cl₂ was added 0.032 ml (0.23 mmol) of triethylamine. This mixture was cooled to −70° C. and isobutyl chloroformate (0.030 ml, 0.23 mmol) was added over a 30 second period. After stirring for 30 minutes at −70° C., the mixture was allowed to warm to 0° C. over a twenty minute period.

(b)

6(R)-[2-[8(S)-(2,2-dimethylbutyryloxy)-2(S)-methyl-6(S)-hydroxymethyl-1,2,6,7,8,8a(S)-hexahydronaphthyl-1(S)]ethyl]-4(R)-hydroxy-3,4,5,6-tetrahydro-2H-pyran-2-one The reaction solution from 1(a) was transferred over a 30 second period to a solution of 8.8 mg of NaBH$_4$ (0.23 mmol) in 2 ml of absolute ethanol, with stirring at 0° C. After 10 minutes the reaction mixture was partitioned between 20 ml of ethyl acetate and 5 ml of 0.1N HCl. The organic phase was separated and subsequently washed with water (2×5 ml) and brine (1×5 ml). After drying (Na$_2$SO$_4$), the solvent was evaporated to give 95 mg of a viscous oil. Chromatography gave the title compound as the major product. TLC behavior and $^1$H-NMR spectra were identical to a sample derived from fermentation.

$^1$H-NMR(CDCl$_3$): delta 0.84 (3H,t,J=7 Hz); 0.91 (3H,d,J=7 Hz); 1.13 (6H,s); 2.62 (1H,m); 2.75 (1H,dd,J=17.5); 3.55 (1H,m); 3.65 (1H,m); 4.38 (1H,m); 5.37 (1H,m); 5.52 (1H,s); 5.80 (1H,m); 6.02 (1H,d,J=10 Hz).

EXAMPLE 2

Preparation of 6(R)-[2-[8(S)-(2,2-dimethylbutyryloxy)-2(S)-methyl-6(S)-hydroxymethyl-1,2,6,7,8,8a(S)-hexahydronaphthyl-1(S)]ethyl]-4(R)-hydroxy-3,4,5,6-tetrahydro-2H-pyran-2-one (a)

6(R)-[2-[8(S)-(2,2-dimethylbutyryloxy)-2(S)-methyl-6(S)-(1-imidazolylcarbonyl)-1,2,6,7,8,8a(R)-hexahydronaphthyl-1(S)]ethyl]-4(R)-hydroxy-3,4,5,6-tetrahydro-2H-pyran-2-one 6(R)-[2-8(S)-(2,2-dimethylbutyryloxy)-2(S)-methyl-6(S)-carboxy-1,2,6,7,8,8a(S)-hexahydronaphthyl-1(S)]ethyl]-4(R)-hydroxy-3,4,5,6-tetrahydro-2H-pyran-2-one (50.4 mg) was dissolved in 0.5 ml of methylene chloride under an atmosphere of nitrogen. The solution was cooled using an ice bath and a solution of carbonyl diimidazole (19.5 mg) in 0.48 ml of methylene chloride was added dropwise and the mixture stirred for 2 hours at the ice bath temperature. Formation of the imidazolide was apparent by $^1$H-NMR(CDCl$_3$) delta 3.85 (1H,m); 7.14 (1H,s) 7.45 (1H,s); 8.15 (1H,s).

(b)

6(R)-[2-[8(S)-(2,2-dimethylbutyryloxy)-2(S)-methyl-6(S)-hydroxymethyl-1,2,6,7,8,8a(S)-hexahydronaphthyl-1(S)]ethyl]-4(R)-hydroxy-3,4,5,6-tetrahydro-2H-pyran-2-one Sodium borohydride (9.7 mg) was added to the reaction solution from example 2(a) followed by 1 ml, of degassed dimethylformamide. After stirring for 30 minutes 1 ml of 1N HCl was added. The reaction mixture was partitioned between 4 ml of ethyl acetate and 10 ml of water. The aqueous phase was then extracted three times with ethyl acetate. All organic extracts were combined, washed with brine three times, dried over anhydrous sodium sulfate and concentrated under vacuum. The resulting oily residue was chromatographed using silica gel (70–230 mesh) and eluted with 1–5% methanol in methylene chloride. The oily product was identical to that obtained in example 1.

What is claimed is:

1. A compound represented by the structural formula (II),

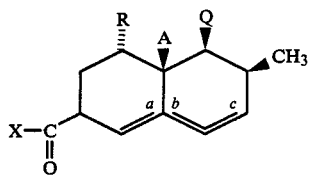

wherein X is selected from: imidazole-1-yl or benzimidazol-1-yl wherein R is

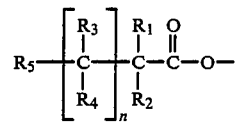

wherein:

n is 0 to 5

R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;

R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 5, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;

R$_5$ is hydrogen, halogen, hydroxy, C$_{1-5}$ alkyl, phenyl or substituted phenyl in which the substituents are V and W, or R$_5$ is a group selected from:

(a) C$_{1-5}$ alkylthio or phenylthio or substituted phenylthio in which the substituents are V and W;

(b) C$_{1-5}$-alkanoyloxy-C$_{1-4}$-alkyl;

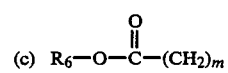

in which m is 0 to 3 and R$_6$ is C$_{1-5}$ alkyl;

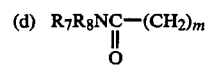

in which R$_7$ and R$_8$ are independently C$_{1-5}$alkyl or R$_7$ and R$_8$ together with the nitrogen atom to which they are attached form a heterocycle selected from piperidinyl, morpholinyl, pyrrolidinyl, piperazinyl or thiomorpholinyl;

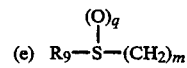

in which q is 0 to 2 and R$_9$ is C$_{1-5}$ alkyl or phenyl or substituted phenyl in which the substituents are V and W;

V and W independently are hydrogen, halogen, hydroxy, trifluoromethyl, C$_{1-3}$ alkyl, C$_{1-3}$alkyloxy and hydroxy-C$_{1-3}$ alkyl; and Q is selected from:

(a) 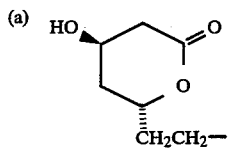

(b) —CH$_2$CH$_2$CN;

(c) 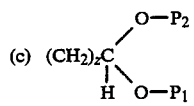

z is 0 to 2 and P$_2$ and P$_1$ are lower alkyl or P$_2$ and P$_1$ together with the oxygens and carbon to which they are attached form a ring of 5 to 8 atoms;
A is H or OH; and a, b and c represent single bonds or one of a, b or c represents a double bond or a and c are both double bonds.

2. A compound of claim 1 wherein Q is

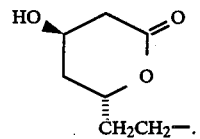

3. A compound of claim 2 wherein a and c represent double bonds.

4. A compound of claim 3 wherein A is H, R$_1$ is methyl, R$_2$ is methyl, n is 1, R$_3$ is hydrogen, R$_4$ is hydrogen and R$_5$ is C$_{1-5}$alkyl.

5. A compound of claim 4 wherein X is

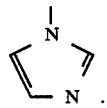

* * * * *